United States Patent [19]

Tsuji et al.

[11] 4,407,959

[45] Oct. 4, 1983

[54] BLOOD SUGAR ANALYZING APPARATUS

[75] Inventors: Nobuhiko Tsuji; Keijiroh Nakamura, both of Yokosuka; Koichi Endoh, Hino; Toshiyoshi Hamada, Sekimachi; Keiichi Ishida, Tokyo, all of Japan

[73] Assignee: Fuji Electric Co., Ltd., Japan

[21] Appl. No.: 313,666

[22] Filed: Oct. 21, 1981

[30] Foreign Application Priority Data

Oct. 29, 1980 [JP] Japan .............................. 55-150756
Dec. 9, 1980 [JP] Japan .............................. 55-172665
Dec. 9, 1980 [JP] Japan .............................. 55-172666

[51] Int. Cl.³ ...................... G01N 35/00; G01N 33/66
[52] U.S. Cl. .................................. 435/288; 204/403; 204/1 T; 364/415; 364/416; 364/497; 435/291; 435/817; 436/50
[58] Field of Search ............... 422/81; 435/288, 289, 435/14, 291, 817; 204/195 B, 1 T; 364/415, 416, 497; 436/50, 55, 34

[56] References Cited

U.S. PATENT DOCUMENTS

| | | | |
|---|---|---|---|
| 3,542,662 | 11/1970 | Hicks | 435/190 |
| 3,770,607 | 11/1973 | Williams | 204/195 B X |
| 3,902,970 | 9/1975 | Levin | 204/195 B X |
| 3,915,644 | 10/1975 | Walraven | 422/81 |
| 3,920,969 | 11/1975 | Berglas | 204/195 B X |
| 3,960,497 | 6/1976 | Acord | 436/50 X |
| 4,224,405 | 9/1980 | Hijikata | 435/288 X |
| 4,240,438 | 12/1980 | Updike | 204/195 B |
| 4,240,889 | 12/1980 | Yoda | 204/195 B |
| 4,266,942 | 5/1981 | Vandenbossche | 364/497 X |
| 4,340,458 | 7/1982 | Lerner | 204/195 B X |
| 4,374,013 | 2/1983 | Enfors | 435/817 X |

Primary Examiner—Sidney Marantz
Attorney, Agent, or Firm—Brumbaugh, Graves, Donohue & Raymond

[57] ABSTRACT

A blood sugar analyzer system for measuring the blood sugar concentration level in a blood specimen is provided. A sensor having a fixed enzyme membrane and a measuring electrode generates a reaction current proportional to the blood sugar level of the specimen, and a sampling mechanism samples the sensor output at regular intervals. A memory receives data from the sampling and divides the data into a group of new data and a group of old data. A calculating mechanism calculates the average value of each group, and the difference between the averages. When the difference exceeds a predetermined value, the latest sensed data value is selected as the rising point of the chemical reaction between the fixed enzyme membrane of the sensor and the blood sugar of the specimen.

3 Claims, 12 Drawing Figures

BLOOD SUGAR ANALYZING APPARATUS

BACKGROUND OF THE INVENTION

1. Field of the Invention

The present invention relates to a blood sugar analyzing apparatus having a fixed glucose oxidase membrane (also known as fixed enzyme membrane).

2. Description of the Prior Art

Blood sugar analyzing apparatus of the type described above measures the blood sugar content or glucose concentration in a blood specimen. The apparatus supplies a blood sugar containing specimen to the enzyme membrane sensor to generate a reaction current proportional to the blood sugar content. The blood sugar analyzing apparatus comprises a fixed enzyme membrane elctrode for measuring the reaction current (a reduction current which flows when reducing hydrogen peroxide is generated upon decomposition of the blood sugar by the fixed enzyme membrane), a reaction cell housing the fixed enzyme membrane electrode and a blood specimen or standard solution (hereinafter referred to as blood specimen or the like), and a liquid pump for drawing a buffer liquid for washing the reaction cell in order to keep the fixed enzyme active.

Figure 1:
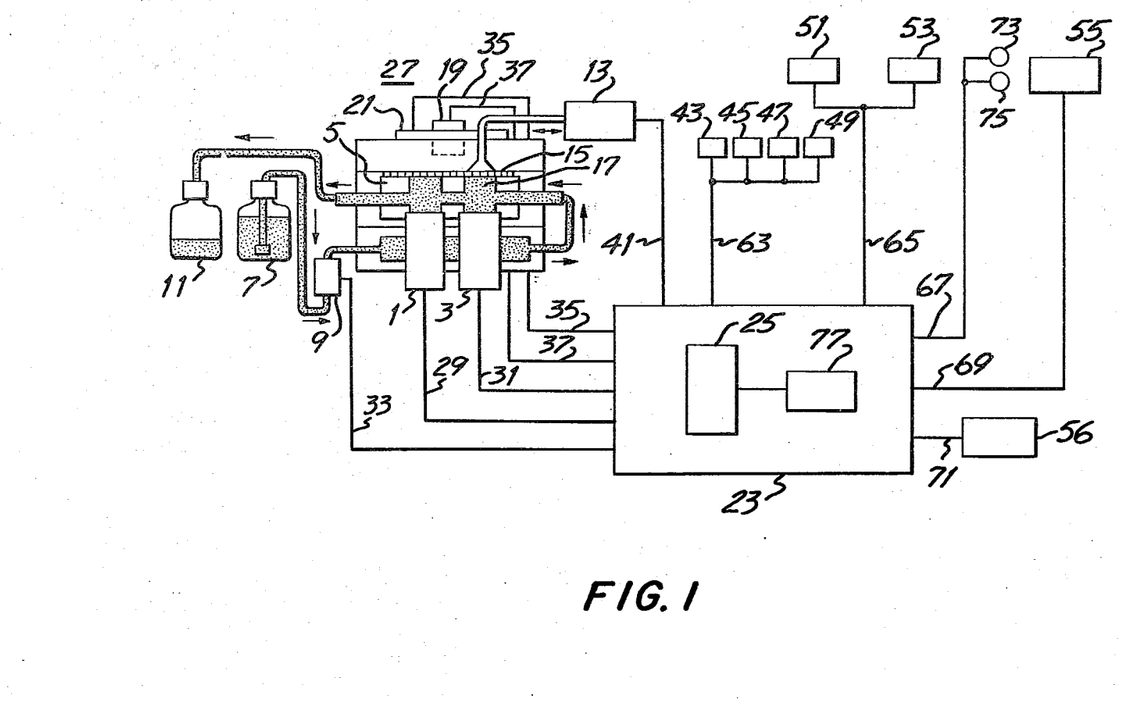
FIG. 1 is a view showing an overall arrangement of a blood sugar analyzing apparatus.

In FIG. 1 a blood sugar measurement electrode or sensor 1 for measuring a reaction current which is proportional to a blood sugar concentration comprises an electrode of platinum and silver having a membrane of glucose oxidase attached to the surface thereof. The blood sugar measurement electrode 1 and a temperature electrode 3 are disposed in a reaction cell 5. A buffer liquid 7 is delivered by a liquid pump 9 into the cell 5 wherein the liquid 7 washes the interior of the cell 5. After the reaction has been finished, the buffer liquid 7 is discharged as a drainage liquid 11. An air pump 13 vibrates a silicon diaphragm 15 to stir a blood specimen which has been introduced through an inlet port 17 into the cell 5, thereby making the concentration of the blood specimen in the cell 5 uniform. A temperature sensor 19 detects the temperature of the cell block. A heater 21 heats the cell block up to about the temperature of a human body (for example, 37° C.), and the blood in the cell 5 is maintained at a temperature equal to a temperature of a human body.

A control device 23 comprised mainly of a microcomputer 25 is connected to a blood sugar analyzing unit 27 through lines 29, 31, 33, 35, 37 and 41. The control device 23 reads out a reaction current from the measurement electrode 1 over the line 29, reads out an amount of temperature compensation with respect to a measured value over the line 29, measures and controls the temperature of the cell block over the lines 35, 37, and controls operation of the liquid pump 9 and the air pump 13 over the lines 33, 41, respectively. The control device 23 is also connected to various switches 43, 45, 47, 49, 51 and 53, a display unit 55, and a printer 56 through lines 63, 65, 67, 69, 71 for controlling input and output devices. Designated at 51 is a specimen number setting switch, 53 is a standard solution value setting switch, 73 and 75 are mode displays for indicating calibration and operation modes, respectively, and switches 43, 45, 47, 49 are mode setting switches for setting for foregoing modes and a paper feed mode for the printer 56, and for setting the switch 51.

The blood sugar analyzing apparatus, while effecting various operations and measurements, goes through several phases such as warming up the apparatus, putting the apparatus on standby, washing the cell, introducing a sample, and washing the cell. More specifically, the sensor is heated up in a "warming-up" phase, the sensor is ready for measurement or awaits a measurement command in "standby", the sensor is washed with the buffer liquid in "washing", the blood sample is introduced or a reaction starting point is detected with transition to a next reaction phase in "sample introduction", and a measured value is converted to a blood sugar concentration and is displayed in "reaction". These phases are indicated by the lighting or flickering of a variety of lamps which let the operator know what phase the apparatus is operating in. To shift the apparatus from one phase to another, it is necessary to detect and judge transient phases or requirements in each phase of the apparatus.

There have heretofore been various problems in detecting phase transitions in the blood sugar analyzers especially when attempting to detect a rising point of a chemical reaction which was started by introducing a blood specimen. It has also been difficult to detect the finishing point of a chemical reaction which converts a reaction current to a corresponding blood sugar concentration.

More specifically, a conventional process of detecting a rising point of a chemical reaction resides in that when a reaction current (which is actually converted to a voltage signal) reaches a predetermined threshold level, the reaction is regarded as being started and is monitored for a given interval of time from that starting point or zero point on. Upon elapse of the given interval of time, for example, 20 seconds, the reaction is regarded as having reached a steady condition, and thereafter a measured value is given by subtracting the threshold value as a base or offset portion from the output of the sensor which increases as the reaction progresses.

The base or offset portion is not necessarily constant and is variable with changes in the condition and temperature in the reaction cell which houses, the enzyme membrane comprising the fixed enzyme membrane and the measuring electrode (the blood sugar analyzing apparatus is particularly affected by temperature changes as it utilizes chemical reactions). If the base or offset portion were rendered constant, the apparatus might erroneously start a measuring operation under some conditions with no blood specimen or the like in the cell, or an excess base portion might be subtracted from a normal reaction quantity, resulting in an incorrect measurement.

According to a process of detecting a reaction ending point, the rising point of the reaction is regarded as a reference point, and the reaction is monitored for a given interval of time from the reference point on, that is, the reaction is assumed to be in equilibrium or finished upon elapse of the given interval of time. Thus, the detection process is dependent only on keeping time.

Figure 2A:
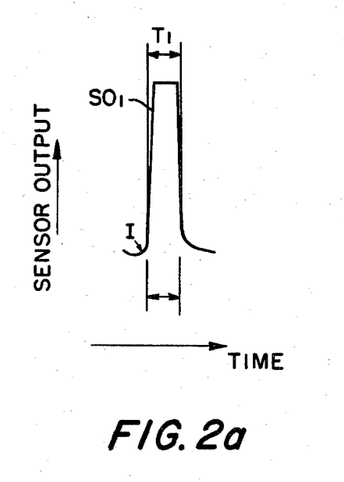
FIG. 2 shows, for comparison, a set of different output characteristic curves of sensors.
Figure 2B:
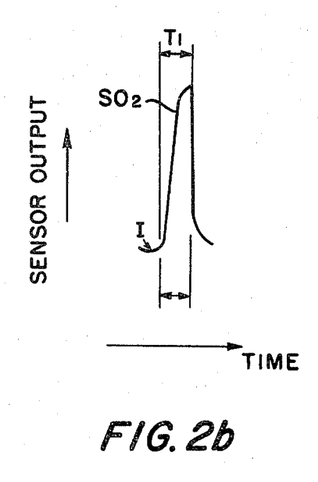

The fixed enzyme membrane in the blood sugar analyzing apparatus tends to deteriorate and its power to measure blood sugar is reduced with the result that changes in the reaction current will become retarded. As can be seen from FIGS. 2, 2(a) and 2(b) the rapid-response sensor has a steeply rising curve $SO_1$ after the blood specimen or the like is introduced at a time I, which the deteriorated sensor gives a less steep curve $SO_2$. Using a deteriorated sensor, simply monitoring a time interval $T_1$ cannot ascertain whether the reaction is saturated, finished or in progress, and hence fails to sense a correct reaction quantity. With the rapid-response sensor, on the other hand, no measurement is effected until the time interval $T_1$ elapses regardless of the sensor's being indicative of saturation or termination of the reaction in a shorter period of time. Accordingly, a time interval in which a measurement should be carried out is wasted, and hence the blood sugar analyzing apparatus has a reduced analyzing capability.

When a blood specimen or the like is introduced in the reaction cell in the blood sugar analyzing apparatus, a reaction with the fixed enzyme starts and reaches a steady condition after a certain period of time (a few seconds) has passed, allowing an analyzed value to be available in proportion to the blood sugar concentration in the blood. The time at which the reaction has reached the steady condition is regarded as a time at which the reaction is ended, and the buffer liquid is delivered into the reaction cell to wash the interior thereof including the enzyme membrane so that the next specimen or a standard solution may be introduced into the cell. The reaction cell has conventionally been washed with a constant amount of buffer liquid during a constant period of time. This washing process is disadvantageous in that a blood specimen of a higher blood sugar content in the reaction cell may not be completely flushed away, and a residual amount of blood sugar may be added to the blood sugar content in a next blood specimen, resulting in a reduced degree of measuring accuracy. To cope with this, the cell is required to be washed again. Where a blood specimen of a lower blood sugar concentration is to be washed away, the buffer liquid required for the washing may be supplied in a smaller amount, and therefore use of the constant amount of buffer liquid for the constant period of time is wasteful.

SUMMARY OF THE INVENTION

It is a first object of the present invention to eliminate the foregoing difficulties in correct measurement by precisely detecting the starting and rising points of a reaction by taking into consideration variations in a base or offset portion.

A second object of the present invention is to obviate the foregoing difficulties for precise measurement by easily and precisely detecting the termination of the reaction.

A third object of the present invention is to remove the above problems by washing the interior of a reaction cell with an optimum amount of buffer liquid which is dependent upon the blood sugar concentration in a blood specimen.

The above objects can be achieved by providing blood sugar analyzing apparatus having a reaction cell which houses an enzyme membrane sensor including a fixed enzyme membrane, and a measuring electrode and which receives a blood specimen, and which causes a chemical reaction for measuring the blood sugar concentration in the blood specimen on the basis of a reaction current generated in the sensor by the chemical reaction, said apparatus having means for sampling an output from said sensor at given intervals of time, means for storing sampled data successively into a memory, means for dividing the stored data into new and old data groups and calculating average values thereof, respectively, and means for calculating the difference between the average values, the arrangement being such that when said difference exceeds a predetermined value, a point at which the latest one of said data is obtained is detected as a rising point of said reaction.

BRIEF DESCRIPTION OF THE DRAWINGS

FIG. 10($a$) is a graph showing a relationship between measuring cycles and analyzed values according to a conventional blood sugar analyzing apparatus; and FIG. 10($b$) is a graph showing a relationship between measuring cycles and analyzed values according to a blood sugar analyzing apparatus of the present invention.

DETAILED DESCRIPTION OF THE INVENTION

The present invention can be described with reference to the accompanying drawings which show several embodiments of the invention.

Figure 3:
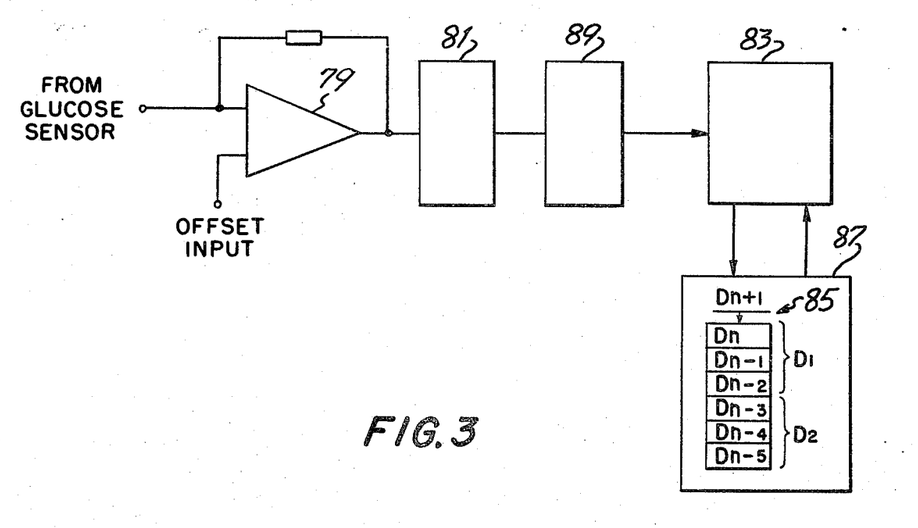
FIG. 3 is a block diagram of an embodiment of the present invention for detecting a rising point.

When a blood specimen or the like is introduced into the reaction cell, the blood sugar measuring electrode or sensor generates a reaction current due to a chemical reaction. As illustrated in FIG. 3 the reaction current is amplified by the differential amplifier 79 and converted to a voltage signal, which is in turn converted by the analog-to-digital converter 81 to a digital signal, which is then fed to the microcomputer 83. The microcomputer 83 samples the output from the sensor at given intervals of time, and sampled data at the time intervals are stored in an area 85 in the RAM memory 87. Assuming that the latest six sampled data ($Dn-5$ to $Dn$) are to be stored, the microcomputer 83 divides these data into new and old groups, that is, the group $D_1$ ($Dn$, $Dn-1$, $Dn-2$) and the old group $D_2$ ($DN-3$, $Dn-4$, $Dn-5$), and calculates respective average values of the groups and a difference between the average values. The difference is considered to be indicative of a change or deviation of a current measured value from a measured value just before the current value. The chemical reaction can safely be regarded as having reached a steady condition when the difference is sufficiently large. Stated otherwise, when the difference exceeds a predetermined value upon comparison, the chemical reaction is regarded as having reached the steady state condition. Where the difference exceeds a predetermined value, the time at which the latest data ($Dn$) out of the six data is obtained is detected as a rising point of the reaction, and the time at which the oldest data ($Dn-5$) is obtained is detected as a starting or zero point of the reaction. When the difference between the average values of the new and old data is negative, the reaction is regarded as being abnormal and no measurement should be made.

Figure 4:
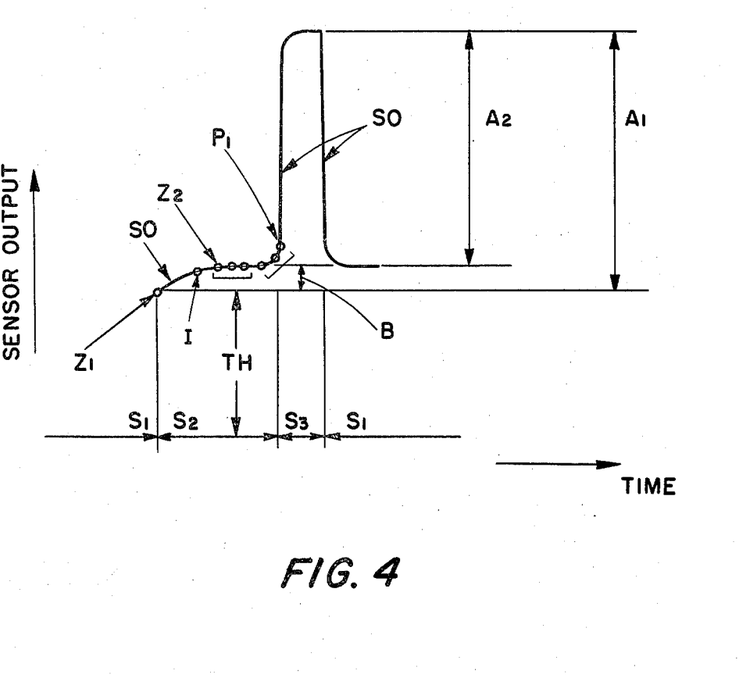
FIG. 4 shows a characteristic curve for the output of a sensor.
Figure 5:
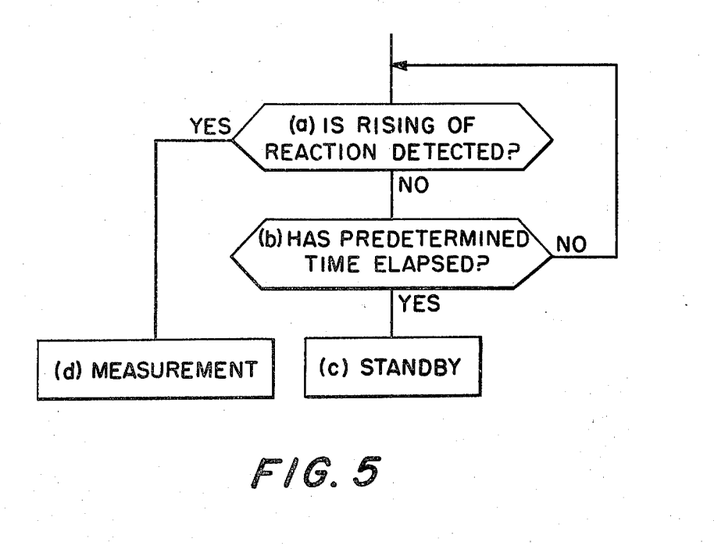
FIG. 5 is a flowchart showing operations of the apparatus of the embodiment shown in FIG. 3.

The foregoing procedure is illustrated in FIG. 4. The sensor output SO varies as shown with time. The blood specimen or the like is introduced at a time I, and the rising point detected according to the present invention is indicated at $P_1$. $Z_2$ denotes the starting or zero point of the reaction. According to the prior process, the zero point is designated at $Z_1$, with the result that a quantity detected by the blood sugar analyzing apparatus, indicated at $A_1$, contains a variation B in the base portion. With the present invention, the blood sugar analyzing apparatus detects a quantity $A_2$ which excludes the variation B in the base portion, and hence enables more precise measurement.

Indicated at TH is a base or offset portion established by the conventional process, and $S_1$ through $S_3$ indicate conditions or operation modes of the analyzer, $S_1$ being indicative of "washing", $S_2$ "introduction", and $S_3$ "measurement".

When the reaction rising point is thus detected, the blood sugar analyzing apparatus now enters the "measurement" mode of operation. However, if deterioration of the enzyme membrane sensor or other causes makes it impossible to detect the reaction rising time, after a predetermined interval of time, the apparatus returns to the "standby" mode of operation.

With the arrangement of the present invention, the arithmetical function of a microcomputer is put to effective use for easy and correct detection of the rising of a chemical reaction, thus enabling a blood sugar analyzing apparatus to effect measurement precisely and reliably.

While in the foregoing embodiment the six sampled data are stored in the random-access memory, it is apparent that the number of data employed and the kind of memory should not be limited to those which are disclosed herein.

Figures 6, 7:
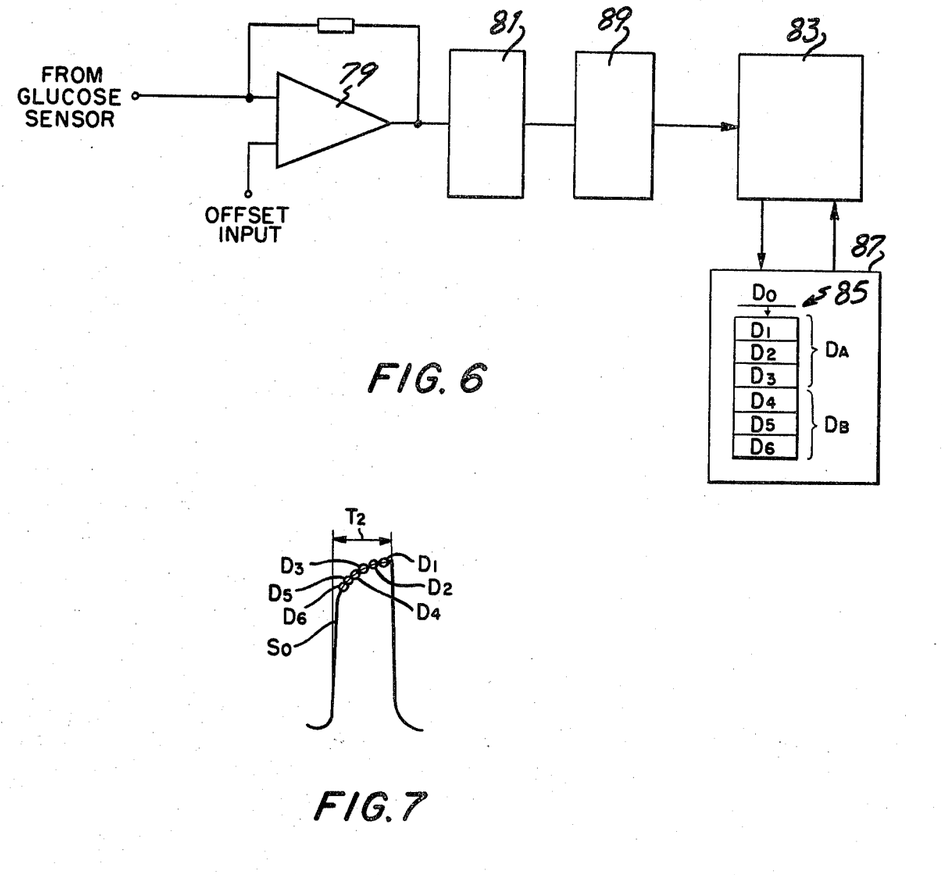
FIG. 6 is a block diagram of an embodiment of the present invention for detecting a finished point.
FIG. 7 shows a characteristic curve of a sensor, explaining a process for detecting a finished point according to the invention.

As shown in FIG. 6, the output of a blood sugar measuring electrode or sensor is supplied to a differential amplifier 79, the output of which is delivered to a microcomputer 83 serving as a control device through an analog-to-digital converter 81 and a buffer 89. A random-access memory is designated as RAM 87.

When a blood specimen or the like is introduced into the reaction cell, the blood sugar measuring electrode or sensor generates a reaction current due to a chemical reaction caused. The reaction current is amplified by the differential amplifier 79 and converted to a voltage signal, which is in turn converted by the analog-to-digital converter 81 to a digital signal, which is then fed to the microcomputer 83. The microcomputer 83 samples the output from the sensor at given intervals of time, and sampled data at the time intervals are stored in an area 85 in the RAM 87. Assuming that latest six sampled data ($D_1$ to $D_6$) are to be stored, the microcomputer 83 divides these data into new and old groups, that is, the group $D_A$ ($D_1$, $D_2$, $D_3$) and the group $D_B$ ($D_4$, $D_5$, $D_6$), and calculates respective average values of the groups and a difference between the average values. The difference is considered to be indicative of a change or deviation of a current measured value from a measured value just before the current value. The chemical reaction can safely be regarded as having been saturated when the difference is sufficiently small. Stated otherwise, when the difference is less than a predetermined value, for example 1 mg/dl, upon comparison, the chemical reaction is regarded as having been terminated. The time at which the newest data $D_1$ out of the six data is obtained is detected as being a reaction finishing point.

The reaction is regarded as having been finished when the difference, either positive or negative, between the average values is less than a predetermined value.

The foregoing process is illustrated in FIG. 7. The output SO from the sensor is sampled at $D_6$–$D_1$ successively in an interval of time $T_2$. The sampled data are processed and subject to the decision procedure as described above.

Figure 8:
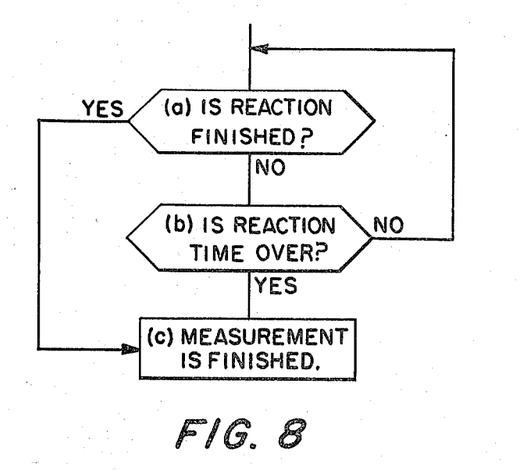
FIG. 8 is a flowchart showing measuring steps according to the present invention.

When the termination of the reaction is thus detected, the sensor output at this time is converted to a corresponding blood sugar concentration value, which is to be displayed. To provide against a slow response of a deteriorated enzyme membrane sensor and an increased period of time required for detection of the reaction termination, a given interval of time is monitored at (b) as shown in FIG. 8. When such a given interval of time has elapsed, the measurement is regarded as having been completed and the apparatus is now allowed to enter a next mode of operation.

While in the foregoing embodiment the six sampled data are stored in the random-access memory, it is apparent that the number of data employed and the kind of memory should not be limited to those which are disclosed herein.

While the processes for detecting reaction rising and finishing points have been described as being applied to a blood sugar analyzing apparatus, the present invention is applicable to a wide variety of analyzing or measuring apparatus which have an enzyme membrane sensor comprising a fixed enzyme membrane and a measuring electrode.

FIG. 1 also serves as a schematic view showing an apparatus which can be washed according to the present invention. Operation according to the present invention will now be described.

Figure 9:
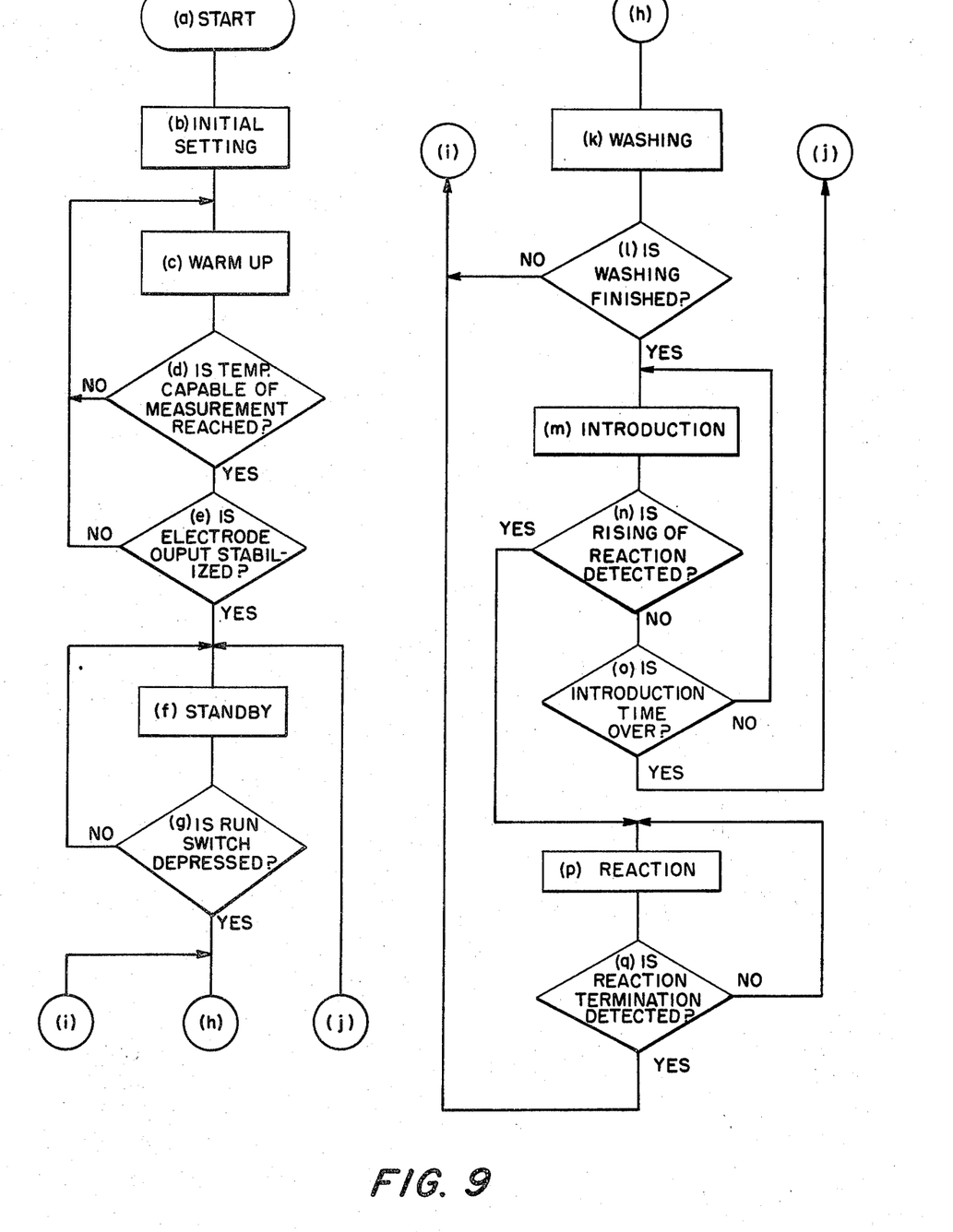
FIG. 9 is a flowchart illustrating operations of the apparatus shown in FIG. 1.

In FIG. 9, when the power supply is turned on to start effecting a measurement at (a), an initial setting of a timer switch and the like is carried out at (b), and the blood sugar analyzing apparatus 27 is warmed up at (c). Upon elapse of a predetermined interval of time required for warming up the apparatus 27, the electrode is heated up to a temperature at which the measurement is possible at (d), whereupon the control device 23 starts monitoring the output from the electrode at (e). When the electrode output is stabilized, the apparatus is ready for the measurement at (f). Unless the electrode is heated to the required temperature or the electrode output is rendered stable, the apparatus continues to operate in the warm-up mode. If the RUN switch 75 and the mode selection switch 49 is depressed at this time at (g), the interior of the cell 5 is washed at (k). After the cell 5 has been washed at (l), a blood specimen or the like is introduced into the cell at (m). Since the apparatus is always calibrated before the blood specimen or the like is measured, a standard solution is first introduced. A chemical reaction with the standard solution is started, and the control device starts reading a reaction current generated on the measuring electrode. The control device detects a rising point of the reaction current at (n), and stores the value of the reaction current at the rising point, which is regarded as being in progress at (p). After a predetermined period of time, 20 seconds, for example, has elapsed, the reaction is regarded as having been terminated at (Q). The cell 5 is washed by a buffer liquid supplied in preparation of a next measurement. The supply of the buffer liquid upon termination of the reaction causes the reaction current to be lowered gradually in level. When it is detected that the level of the reaction current coincides with the current level stored at the rising point, or that the rate of change at which the current level decreases (a change in the reaction current/time=tan $\theta$) falls to zero, the control device 23 stops the supply of the buffer liquid, thus completing the washing of the cell. The blood sugar analyzing apparatus is thereafter calibrated by making a plurality of measurements of standard solutions. After the calibration has been over, a blood specimen is measured in a manner described above. The measurement is carried out once, and the result of the measurement is corrected automatically by the above calibration data and displayed on the display 55.

The manner in which the blood sugar analyzing apparatus of the present invention improves the relationship between measuring cycles and anlyzed values will be described by way of comparison with a conventional arrangement.

Figure 10A:
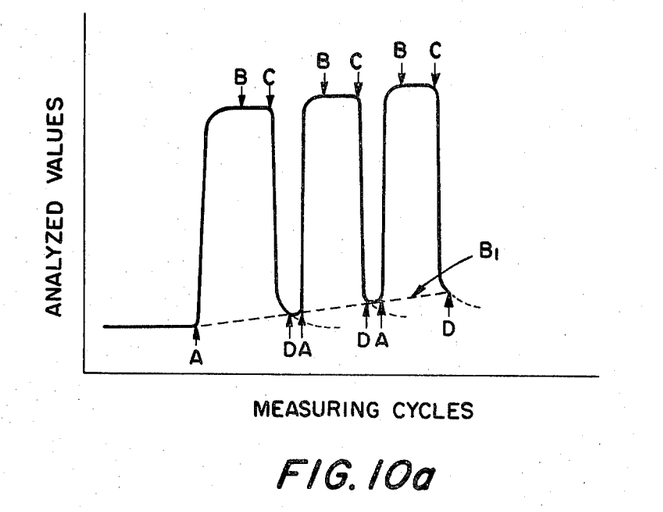
Figure 10B:
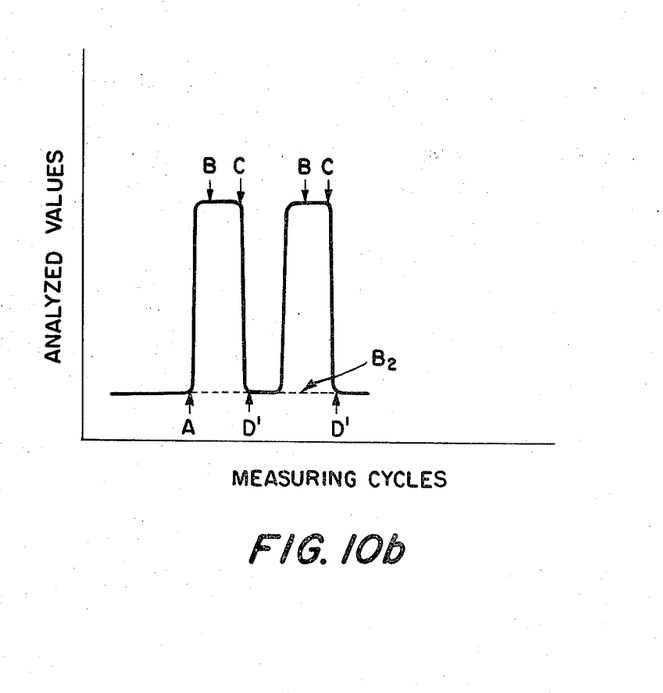

With reference to FIGS. 10(a) and 10(b) designated at A is a time at which a blood specimen or the like is introduced into the cell, B a time at which the reaction is in a steady condition or is terminated, C a time at which the cell starts being washed, D a time at which the washing of the cell is finished, $B_1$ and $B_2$ reference lines for the analyzed values. A comparison between these graphs shows that the reference line $B_1$ for the analyzed values produced by the conventional apparatus is gradually raised or inclined upwardly through the measuring cycles due to added increments resulting from unwashed blood sugar, while the reference line $B_2$ according to the blood sugar analyzing apparatus remains steady without affecting the measurement of a next blood specimen, resulting in an improved degree of measuring accuracy.

The blood sugar analyzing apparatus of the present invention has a tendency for the current level after the cell has been washed to fail to get steady or reach the level at the rising point, allowing continued washing of the cell. To cope with this problem, the apparatus has an added function to stop washing of the cell a predetermined time interval, for example, 30 seconds, after the washing has started. Decision and control for such a function is effected by the control device 23.

With the present invention, the cell is washed in accordance with the blood sugar concentration in a blood specimen or the like that has been measured to avoid accumulation of unwashed blood sugar. Thus, the blood sugar analyzing apparatus is subjected to less measuring errors and hence has an increased degree of measuring accuracy. A blood specimen of a low blood sugar content can be washed away in a short period of time with a smaller amount of buffer liquid than would be necessary in conventional blood sugar analyzing apparatus.

We claim:

1. A blood sugar analyzing apparatus for analyzing the blood sugar concentration in a blood specimen, comprising:
 a reaction cell which houses an enzyme membrane sensor including a fixed enzyme membrane and a measuring electrode, said cell having means for receiving a blood specimen in contact with said sensor to thereby cause a chemical reaction to occur between the specimen and the membrane, and wherein the measuring electrode produces a reaction current in response to the chemical reaction;
 means for sampling an output from said sensor at given intervals of time;
 means for storing data representing the sampled outputs;
 processing means for separating the stored data into new and old data groups, for calculating the average data values of said new and old data groups and for calculating the difference between the average data values, and for determining a background offset portion of the reaction current at a first time point when said difference exceeds a first predetermined value and for determining a steady state level of the reaction current at a second time point, after said first time point, when the difference does not exceed a second predetermined value, and for calculating a blood sugar concentration level of the specimen which is proportional to the difference between the steady state level and the background offset portion of the reaction current.

2. A blood sugar analyzing apparatus for analyzing the blood sugar concentration in a blood specimen, comprising:
 a reaction cell which houses a fixed enzyme membrane and a measuring electrode, said cell having means for receiving a blood specimen to thereby cause a chemical reaction between said blood specimen and said fixed enzyme membrane for measuring the blood sugar concentration in said blood specimen on the basis of a reaction current generated in said measuring electrode by the chemical reaction, said reaction cell also having means for receiving a buffer liquid supplied each time said chemical reaction is terminated so as to be washed thereby; and
 control means for detecting a rising point of said reaction current when said blood specimen is introduced into said reaction cell, for storing the current level from the measuring electrode at that time, for detecting when the reaction has terminated, for supplying said buffer liquid to said cell after the reaction has been terminated, and for stopping the supply of said buffer liquid when said reaction current level returns to the level of said rising point.

3. A blood sugar analyzing apparatus for analyzing the blood sugar in a blood specimen, comprising:
 a reaction cell which houses an enzyme membrane sensor including a fixed enzyme membrane and a measuring electrode, said cell also having means for receiving a blood specimen in contact with said sensor to thereby cause a reaction current to be generated in the measuring electrode in response to a chemical reaction between the specimen and membrane;
 means for determining the rising point of the reaction and for determining a background offset portion of the reaction current at a first time point;
 means for determining a steady state value of the reaction current at a second time point, after said first time point; and
 means for calculating a blood sugar concentration level of said specimen which is proportional to the difference between said steady state value and said background offset value.

* * * * *